United States Patent
Geoghegan et al.

(10) Patent No.: US 6,641,839 B1
(45) Date of Patent: Nov. 4, 2003

(54) PHARMACEUTICAL FORMULATIONS FOR PREVENTING DRUG TOLERANCE

(75) Inventors: Edward James Geoghegan, Athlone (IE); Seamus Mulligan, Athlone (IE); Mary Margaret Foynes, Athlone (IE)

(73) Assignee: Athpharma Limited, Roscommon (IE)

(*) Notice: Subject to any disclaimer, the term of this patent is extended or adjusted under 35 U.S.C. 154(b) by 407 days.

(21) Appl. No.: 08/797,318

(22) Filed: Feb. 7, 1997

Related U.S. Application Data

(63) Continuation of application No. 08/419,520, filed on Apr. 10, 1995, which is a continuation of application No. 08/320,599, filed on Oct. 11, 1994, which is a continuation of application No. 07/823,597, filed on Jan. 17, 1992, now abandoned, which is a continuation of application No. 07/273,217, filed on Nov. 18, 1988, now abandoned.

(30) Foreign Application Priority Data

Nov. 20, 1987 (IE) .............................................. 3157/87

(51) Int. Cl.$^7$ ................................................ A61K 9/24
(52) U.S. Cl. ..................................................... 424/473
(58) Field of Search ......................................... 424/473

(56) References Cited

U.S. PATENT DOCUMENTS

| | | | |
|---|---|---|---|
| 4,291,015 A | | 9/1981 | Keith et al. |
| 4,336,243 A | | 6/1982 | Sanvordeker et al. |
| 4,369,172 A | * | 1/1983 | Schor .................... 424/19 |
| 4,615,699 A | | 10/1986 | Gale et al. |
| 4,655,766 A | | 4/1987 | Theeuwes et al. |
| 4,663,150 A | | 5/1987 | Panoz et al. |
| 4,681,584 A | | 7/1987 | Gale et al. |
| 4,698,062 A | | 10/1987 | Gale et al. |
| 4,721,619 A | * | 1/1988 | Panoz et al. ................. 424/459 |
| 4,767,808 A | * | 8/1988 | Kydonieus et al. ............ 524/98 |
| 4,800,084 A | * | 1/1989 | Zerbe ......................... 424/458 |
| 4,863,742 A | * | 9/1989 | Panoz et al. ................. 424/473 |
| 4,938,967 A | * | 7/1990 | Newton et al. ............... 424/458 |
| 5,071,656 A | | 12/1991 | Lee et al. ................... 424/448 |
| 5,141,750 A | | 8/1992 | Lee et al. ................... 424/448 |

FOREIGN PATENT DOCUMENTS

| | | | |
|---|---|---|---|
| EP | 0159168 | 10/1985 | |
| EP | 0163000 | 12/1985 | |
| EP | 207397 | 1/1987 | .......... A61K/31/44 |
| EP | 0250267 | 12/1987 | |
| EP | 290262 | 11/1988 | ............ A61K/9/70 |
| JP | 59 84820 | 5/1984 | |
| JP | 62126127 | * | 6/1987 |

OTHER PUBLICATIONS

"Isosorbide–5–Nitrate sustained–release pellets—an example of computer supported drug development", Zerbe et al., Pharmacuetical Resarch 1985, No. 1, Jan., pp. 30–36.
"Glyceryl trinitrate (nitroglycerine) and the Organic nitrates choosing the method of administration", J. Abrahms, Drugs 34: 391–403 (1987).
"Dose Dependence of Tolerance during treatment with mono–nitrates", M. Tauchert et al., Z. Cardiol. 72, Suppl. 3, 218–228 (1983).
"Tolerance Development during isosorbide dinitrate treatment: Can it be circumvented?", W. Rudolf et al., Z. Cardiol. 72, Supple. 3, 195–198 (1983).
"Anti–ischemic effects of 80mg tablet of isosorbide dinitrate in sustained–release form before and after two weeks treatment with 80mg once daily or twice daily", S.Silver et al., Z.Cardiol. 72, Suppl. 3, 211–217 (1983).
"Hemodynamic measurements and excercise testing to assess the development of tolerance against slow–release isosorbide dinitrate", H. Weidemann et al., Z.Cardiol.72, Suppl. 3, 229–232.
"Tolerance to isosorbide dinitrate: rate of development and reversal", J.Parker et al., Circuation vol. 86, No. 5, 11/83.
"Nitrate Tolerance", Leier, Amer. Heart Journ., 7/85, 224–232.
"Effect of Intervals between doses on the development of tolerance to lisosorbide dinitrate", Parker et al., the New England Journal of Medicine, Jun. 4, 1987, pp. 1140–1444.
"Pharmacology of Nitroglycerine and long–acting nitrates", J. Abrahms, American Journ. of Card., vol. 56, 7/85, pp. 12a–18a.
"New nitroglycerine formulations: Transdermal and Transmucosal nitroglycerine", J. Abrahms, Z. Caridol, 74. Suppl. 4. 10–15 (1985).
Chem. Abstracts 101:78879s "Sustained–release transdermal tapes" corresponding to Kokai Koho JP 59–85820, May 16, 1984.

* cited by examiner

Primary Examiner—Russell Travers
(74) Attorney, Agent, or Firm—Finnegan, Henderson, Farabow, Garrett & Dunner, L.L.P.

(57) ABSTRACT

Isosorbide mononitrate formulations and methods of treatment are disclosed. The formulations and treatments provide for subtherapeutic levels of the mononitrate in a washout period to prevent nitrate tolerance.

18 Claims, No Drawings

PHARMACEUTICAL FORMULATIONS FOR PREVENTING DRUG TOLERANCE

This disclosure is a continuation of patent application Ser. No. 08/419,520, filed Apr. 10, 1995, which is a continuation of patent application Ser. No. 08/320,599, filed Oct. 11, 1994, which is a continuation of patent application Ser. No. 07/823,597, filed Jan. 17, 1992, now abandoned, which is, itself, a continuation of patent application Ser. No. 07/273,217, filed Nov. 18, 1988, now abandoned.

BACKGROUND OF THE INVENTION

This invention relates to isosorbide mononitrates (ISMN) and the use thereof in the preparation of ISMN-containing pharmaceutical formulations which allow one to achieve a controlled absorption of ISMN in vivo. The invention relates, in particular, to an ISMN formulation suitable for once-daily administration, which circumvents the tolerance and attenuation problems commonly observed in nitrate therapy.

Isosorbide mononitrates are vasodilators and arterial dilators, and by these actions in patients with angina pectoris reduce myocardial oxygen demands while maintaining or increasing coronary artery flow. The organic nitrate vasodilator, isosorbide dinitrate (ISDN) which is used in the treatment of angina pectoris has two major mononitrate metabolites, isosorbide-5-mononitrate (IS-5-MN) and isosorbide-2-mononitrate (IS-2-MN). It is now widely accepted that these metabolites are themselves pharmacologically active and IS-5-MN is now used in the treatment of angina pectoris in several countries. It is also thought that both metabolites contribute to the time course and character of response to ISDN. While ISDN has been used successfully for many years in the prophylaxis of angina pectoris and as adjunctive therapy in congestive heart failure, the discovery that it functions to a significant extent as a prodrug has led to an increase in the direct administration of ISMN for the same therapeutic indications. Unlike the parent substance (ISDN), ISMN does not undergo first-pass metabolism in the liver, thus providing for an overall greater systemic bioavailability of the mononitrate dose. ISMN is also completely absorbed from the gastrointestinal tract after oral administration and has a much longer half-life than ISDN. It has also been discovered by the Applicants that ISMN is absorbed through the skin, thus enabling one to achieve the desired plasma levels by administering ISMN transdermally.

These factors make ISMN a more attractive form of nitrate therapy for the management of angina and also for the development of long-acting oral nitrate formulations which serve to increase patient compliance, concomitantly indirectly increasing the therapeutic efficacy of nitrates in the population at large. Once-daily administration of ISMN offers many advantages over conventional more frequently administered forms. One of the main advantages is the increased patient compliance which is gained as a result of less frequent administration. It has been demonstrated that with once-a-day administration of a drug, patient compliance can be as high as 80%, while with twice-a-day and three times-a-day dosing, compliance levels can fall to 60% and 40% respectively. Thus, it is obvious that any reduction of dosage frequency can only serve to provide a therapeutic benefit to the patient. Another advantage offered by once-a-day dosing is the potential to reduce the incidence of side effects caused by the high-peak/low-trough plasma profile observed with more frequently administered drugs.

While this ambition has been realised with the recent introduction of ISMN formulations for once-daily administration in several countries, a remaining problem in nitrate therapy has not yet been addressed, this problem being nitrate tolerance and attenuation.

The issue of once-daily nitrate therapy was first addressed with the advent of transdermal nitroglycerin administration. Sustained release transdermal preparations of ISDN have since followed. However, it has been found that tolerance can develop extremely quickly to such transdermal systems and patients have been shown to achieve only minimal increases in exercise tolerance after 24 hours of transdermal nitrate administration. (AM J. Cardiol 1985;56:281–311). (The ability to increase a patient's capacity for exercise without onset of anginal symptomology is a major clinical criterion for determining the efficacy of anti-anginal agents).

Nitrate tolerance may be defined as that condition where the haemodynamic responsiveness of the target tissue is lost. Whilst the direct cause of nitrate tolerance is still a matter of some speculation, it is suspected that it may be due to changes in pharmacokinetics or to alterations in the property of target tissues such as the arterial and venal smooth muscle, making them less sensitive or refractory to the nitrate effect.

Nitrate therapy is the oldest treatment modality for angina pectoris and the phenomenon of nitrate tolerance has been observed in humans with all commonly used nitrates, regardless of the method or route of administration. This problem is as much a part of ISMN administration as with any other nitrate, and so to maximise the undoubted beneficial effects and recognised advantages of ISMN, it is necessary to design a formulation which overcomes the tolerance effect. ISMN, both in conventional (administered 10–40 mg two to three times daily) and sustained release (20–60 mg one to two times daily) forms achieves initial beneficial effects, but during the course of continued therapy, there is a marked attenuation of the effect in both magnitude and duration whereby the maximum therapeutic benefit can only be maintained by gradually increasing the dosage. The occurrence of this nitrate attenuation in patients suffering from such serious conditions as chronic angina pectoris is clearly undesirable, and requires constant monitoring and re-titration to safely manage the patient.

The ideal concept or model for an efficacious once-daily drug is one which provides constant blood levels in the therapeutic range over 24 hours. However, in the case of chronic nitrate therapy, maintenance of such constant levels over 24 hours, regardless of the route or frequency of administration, have been directly linked to the development of tolerance. Therefore, the ideal model does not hold true in the case of nitrates. Haemodynamic studies conducted to date suggest that short periods of nitrate withdrawal restore the haemodynamic and therapeutic effect of the nitrates. In this manner, the concept arose of allowing a washout period for a portion of the day, where the nitrate plasma concentration is allowed to fall below certain critical levels. With the conventional orally administered nitrates, it appears desirable to administer on a two or three times-a-day basis, omitting the final dose in the evening to allow a washout period or in the case of a transdermal device, to remove it after 12 or more hours following application: However, with the currently available once- and twice-a-day ISMN products, the simple withdrawal of one of the doses becomes impossible or in the case of the twice-a-day product, potentially dangerous as the patient would have sub-therapeutic levels for at least 12 hours. With ISMN and nitrates in general, the most effective duration for the washout period is suggested as being somewhat less than 12 hours. A washout phase occurs during which the concentrations fall precipitously (preferably with a peak-to-trough ratio of 6:1 or greater) and below critical minimum levels (100 ng/ml approx. for IS-5-MN and 20 ng/ml approx. for IS-2-MN).

SUMMARY OF THE INVENTION

Therefore, it is an object of the present invention to provide a formulation of a drug such as ISMN for once-daily administration, which is characterised by a high degree of absorption, which achieves significant and therapeutic plasma levels of the drug which are maintained for an extended period after administration, and which exhibits a controlled reduction in plasma levels sufficient to prevent or reverse drug tolerance.

In nitrate therapy, it is now widely believed that there is a critical minimum plasma level, above which one gets beneficial clinical effect, and below which one prevents nitrate tolerance. The minimum critical plasma concentration for therapeutic effect is, as indicated above, approximately 100 ng/ml for IS-5-MN and approximately 20 ng/ml for IS-2-MN, which is pharmacologically more active than the IS-5-MN metabolite. It is desirable to fall below these levels for a certain period of the day, preferably less than 12 hours and ideally for 6–10 hours, in order to prevent tolerance.

Additionally, it has been proposed that the rate of fall off of plasma ISMN levels during the washout phase may be critical for the reversal of tolerance, for example a peak-to-trough ratio (i.e. a peak concentration to 24 hour concentration ratio) equal to or greater than 6:1 may be desirable. Accordingly it is an object of the present invention to provide ISMN formulations and a method of treatment which prevent tolerance by these means.

It is an object of the present invention to provide a controlled absorption form of ISMN which is suitable for once daily administration, which is characterised by a high degree of absorption, which achieves therapeutic plasma levels of ISMN which are maintained for an extended period after administration, which exhibits controlled reduction in plasma levels sufficient to prevent tolerance.

It is another object of the present invention to provide a controlled absorption form of ISMN for oral administration which achieves reversal of nitrate tolerance as discussed above.

A further object of the present invention is to provide a controlled absorption form of ISMN for transdermal administration which achieves reversal of nitrate tolerance as discussed above.

Accordingly, the invention provides a controlled absorption ISMN containing pellet formulation for oral administration, said pellet comprising:

i) a core of
  (a) a powder mixture containing an ISMN or a pharmaceutically acceptable salt thereof and optionally one or more excipients selected from an organic acid or base and a pharmaceutically acceptable diluent, and
  (b) a polymeric material containing a major proportion of a pharmaceutically acceptable water soluble polymer and optionally a minor proportion of a pharmaceutically acceptable water insoluble polymer,
  said core comprising layers of said powder mixture and said polymeric material superimposed one upon the other and said polymeric material being present in an amount effective to ensure that all of said powder mixture is coated onto said core; and ii) a multi-layer membrane surrounding said core and containing a major proportion of a pharmaceutically acceptable film-forming, water-insoluble polymer and optionally a minor proportion of a pharmaceutically acceptable film-forming, water-soluble polymer,
  the number of layers in said membrane and the ratio of said water-soluble polymers to said water-insoluble polymers being effective to permit release of said ISMN from said pellet at a rate allowing controlled absorption thereof over a 24 hour period following oral administration, said rate being measured in vivo and having a Tmax between 2 and 10 hours and achieving minimum effective blood levels from 12 to 20 hours over a 24 hour period.

Preferably, minimum effective blood levels are achieved from 14 to 18 hours over a 24 hour period. Occasionally a T-max of greater than 10 hours can be achieved depending on individual absorption rates.

Suitable organic acids defining the optional excipient of the core are selected from adipic acid, ascorbic acid, citric acid, fumaric acid, malic acid, succinic acid and tartaric acid or a mixture thereof.

Suitable organic bases defining the optional excipient of the core are sodium citrate, sodium succinate, sodium tartrate, potassium citrate, potassium tartrate, potassium succinate or a mixture thereof.

Suitable pharmaceutically acceptable diluents defining the optional excipient of the core are selected from lactose, talc, microcrystalline cellulose, sorbitol, mannitol, xylitol, fumed silica, stearic acid, magnesium stearate and sodium stearate or a mixture thereof.

The ISMN is isosorbide-2-mononitrate or isosorbide-5-mononitrate.

ISMN is widely used in anti-anginal therapy and the patient for one reason or another (for example, takes the dose later than due, is switching from conventional frequently administered immediately released products, etc.) may require a rapid attainment of effective therapeutic blood levels for fast relief of onset of anginal attack.

Accordingly, the invention further provides a controlled absorption ISMN formulation for oral administration comprising a blend of pellets as hereinbefore specified in admixture with a rapidly releasing form of ISMN to ensure a rapid attainment of effective therapeutic blood levels of ISMN within 3 hours following administration. The said rapidly releasing form may be active ingredient itself or rapidly releasing pellets as hereinbefore specified without said multi-layer membrane.

The formulations according to the invention are preferably administered in a manner where the washout phase occurs during a period of prolonged inactivity or minimum risk period for the patient, such as sleeping time. This ensures that the lowest plasma levels of ISMN coincide with the period of least physical stress on the patient.

The ISMN component and excipient if present are preferably present in a ratio of from 1:4 to 50:1.

As used herein the term water-soluble polymer is intended to include polymers which are freely water permeable and porous polymers. The term water-insoluble polymer as used herein is intended to include polymers which are slightly water permeable or water impermeable and non-porous polymers.

The polymeric material may consist solely of a water soluble polymer or a polymer which is freely permeable to ISMN and water. Alternatively, the polymeric material of the core may include a minor proportion of a water insoluble polymer or a polymer which is slightly permeable to ISMN and water. The ratio of water soluble/freely permeable to water insoluble/slightly permeable polymer is determined by the particular combination of polymers selected.

The water soluble polymer is suitably polyvinyl alcohol, polyvinylpyrrolidone, methyl cellulose, hydroxypropyl cellulose, hydroxypropylmethyl cellulose or polyethylene glycol or a mixture thereof. An especially preferred water soluble polymer is polyvinylpyrrolidone.

A suitable polymer which is freely permeable to ISMN and water is a polymer sold uder the Trade Mark EUDRAGIT RL.

The water insoluble polymer is suitably ethylcellulose, cellulose acetate, cellulose propionate (lower, medium or higher molecular weight), cellulose acetate propionate, cellulose acetate butyrate, cellulose acetate phthalate, cellulose triacetate, poly (methyl methacrylate), poly(ethyl methacrylate), poly (butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly (ethylene terephthalate), poly(vinyl isobutyl ether), poly (vinyl acetate), poly(vinyl chloride) or polyurethane or a mixture thereof.

A suitable polymer which is slightly permeable to ISMN and water is a polymer sold under the Trade Mark EUDRAGIT RS.

Other suitable polymers which are slightly permeable to ISMN and water and whose permeability is pH dependent are sold under the Trade Marks EUDRAGIT L, EUDRAGIT S or EUDRAGIT E.

EUDRAGIT polymers are polymeric lacquer substances based on acrylates and/or methacrylates.

Polymeric materials sold under the Trade Marks EUDRAGIT RL and RS are acrylic resins comprising copolymers of acrylic and methacrylic acid esters with a low content of quaternary ammonium groups and are described in the "EUDRAGIT" brochure of Messrs. Rohm and Haas (1985) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

EUDRAGIT L is an anionic polymer synthesized from methacrylic acid and methacrylic acid methyl ester. It is insoluble in acids and pure water. It becomes soluble in a neutral to weakly alkaline milieu by forming salts with alkalis. The permeability of EUDRAGIT L is pH dependent. Above pH 5.0, the polymer becomes increasingly permeable. EUDRAGIT L is described in the "EUDRAGIT L' brochure of Messrs. Rohm Pharma GmbH (1986) wherein detailed physical-chemical data of the product are given. EUDRAGIT E and S are also described in the "EUDRAGIT E" and "EUDRAGIT S" brochures, respectively, of Messrs. Rohm Pharma GmH (1986).

Preferably, the multi-layer arrangement of ISMN, optional excipient and polymeric material is built up on a central inert core, suitably consisting of a non-pareil seed of sugar or starch having an average diameter in the range of 0.3–0.8 mm, especially 0.4–0.7 mm in a conventional coating pan or, alternatively, using an automated system such as a CF granulator, for example, a FREUND CF granulator, a GLATT fluidized bed processor, an AEROMATIC, a modified ACCELA-COTA or any other suitably automated bead coating equipment (FREUND, GLATT, AEROMATIC and ACCELA-COLA are all Trade Marks).

The core may also include components such as a lubricant, a dispersing agent, a plasticizer or a surfactant. A suitable and particularly preferred lubricant is talc or magnesium stearate and a suitable surfactant is sodium lauryl sulphate. A plasticizer is chosen depending on the polymer used, for example, tributyl citrate is a suitable plasticizer for EUDRAGIT RS and EUDRAGIT RL and dibutyl sebecate is a suitable plasticizer for cellulose acetate and cellulose acetate phthalate.

The ISMN or pharmaceutically acceptable salt thereof, optional excipient and optionally other components as described hereinbefore are blended to form a homogenous powder. The blend is suitably passed through a No. 25–400 mesh screen, normally a No. 50–100 mesh screen using a milling machine. Alternatively, the excipient and/or other components can be blended together and milled, with the resulting mixture then blended together with ISMN or a pharmaceutically acceptable salt thereof. Alternate layers of a coating solution/suspension of the polymeric material and the powder are applied to the central inert core so as to build up the multi-layer arrangement of the active core. The coating solution/suspension of the polymeric material comprises one or more polymers dissolved/suspended in a suitable solvent or mixture of solvents. The solvent system may be organic or aqueous. The concentration of the polymeric material in the coating solution/suspension is determined by the viscosity of the final solution. A suitable plasticizer as described previously may be added to the coating solution/suspension. Especially preferred coating solutions/suspensions include:

a. 10% polyvinylpyrrolidone in isopropanol or ethanol;
b. 10% ethyl cellulose in isopropanol;
c. 5% hydroxypropylmethyl cellulose in methanol/methylene chloride 60/40;
d. 5% EUDRAGIT RL in isopropanol/acetone 60/40;
e. 5% EUDRAGIT RS in isopropanol/acetone 60/40;
f. 30% EUDRAGIT RS water dispersion; and
g. 30% EUDRAGIT RL water dispersion.

On completion of the application of the core-forming materials the active cores are dried in a conventional drying oven at a temperature of from 35–65° C., preferably 40–60° C. Alternatively, other types of conventional pharmaceutical drying equipment can be used such as fluid bed, vacuum and microwave.

The membrane of the film-forming polymer or mixture of polymers surrounding the core has a major proportion of a water insoluble polymer and optionally a minor proportion of a water soluble polymer as hereinbefore defined, the ratio of water insoluble to water soluble polymer being determined by the inherent solubility characteristics of the polymers selected.

The water insoluble polymer of the membrane is any one of those hereinabove specified for the core and includes polymers which are slightly permeable or impermeable to ISMN and water as hereinabove indicated.

Likewise the water soluble polymer of the membrane is any one of those hereinabove specified for the core and includes polymers which are freely permeable to ISMN and water as hereinabove indicated.

On completion of the application of the coating solution/suspension the pellets are dried in a conventional drying oven at a temperature of from 35–65° C., preferably 40–60° C. Alternatively, other types of conventional pharmaceutical drying equipment can be used, such as fluid bed, vacuum and microwave.

The invention further provides a preparation for the once-daily, percutaneous administration of ISMN or a pharmaceutically acceptable salt thereof which comprises ISMN or a pharmaceutically acceptable salt thereof uniformly distributed in a solid, semi-solid or mucilaginous medium which,can be placed in intimate contact with the skin, preferably said solid, semi-solid or mucilaginous medium being formed by adding a given amount of ISMN or a pharmaceutically acceptable salt thereof to a solution of a solidifying or gel-forming agent or mixture thereof in a suitable solvent or mixture of solvents and mixing or heating the mixture thereby obtained so as to form said solid, semi-solid or mucilaginous medium, the release of said ISMN or pharmaceutically acceptable salt thereof from said preparation being at a rate allowing controlled absorption thereof over a 24 hour period following topical application of said preparation, said rate being measured in vivo and having a Tmax between 2 and 16 hours and achieving minimum effective blood levels from 12 to 20 hours over a 24 hour period.

The term solidifying agent as used herein also embraces thickening, hardening, setting, suspending or like agents.

Suitable materials for use as the solidifying or gel-forming agent according to the invention include, for example, plant extracts, vegetable oils, gums, synthetic or natural polysaccharides, polypeptides, alginates, hydrocarbons, synthetic polymers, minerals and silicon compounds and mixtures thereof.

Suitable plant extracts include agar, ispaghula, psyllium, cydonia and ceratonia or a mixture thereof.

A suitable vegetable oil is hydrogenated castor oil.

Examples of suitable gums include guar gum, acacia gum, ghatti gum, karaya gum, tragacanth gum and xanthan gum or a mixture thereof.

Suitable synthetic and natural polysaccharides include alkylcelluloses, hydroxyalkylcelluloses, cellulose ethers, cellulose esters, nitrocelluloses, dextrin, agar, carrageenan, pectin, furcellaran and starch or starch derivatives and mixtures thereof. An example of a preferred starch derivative is sodium starch glycolate. Especially preferred polysaccharides include agar and carrageenan.

Other suitable synthetic polymers include polyvinylpyrrolidone and polymeric lacquer substances based on acrylates and/or methacrylates sold under the Trade Mark EUDRAGIT. An especially preferred synthetic polymer is a carboxyvinyl polymer sold under the Trade Mark CARBOMER.

Suitable polypeptides include zein, gelatin, collagen and polygeline or a mixture thereof.

Suitable alginates include alginic acid, propylene glycol alginate and sodium alginate or a mixture thereof.

Preferred hydrocarbons include soft paraffin and hard paraffin, especially white petrolatum.

Suitable minerals include bentonite, hectorite, aluminium magnesium silicate and magnesium silicate or a mixture thereof.

Suitable compounds based on silicon include colloidal silicon dioxide, silicones, polysiloxanes and silica gels or a mixture thereof.

The term "agar" is used throughout the Specification and is synonymous with "agar-agar".

The solvent used may suitably be water or an alcohol such as ethanol or stearyl alcohol, glycerol, propylene glycol, polyethylene glycol or silicone or a mixture thereof, including a mixture with water. Preferably the solvent used is a water and alcohol mixture.

The preparation when in the form of a solid or semi-solid preferably has a surface area in the range 2 to 15 cm$^2$, more especially 5 to 10 cm$^2$.

The thickness of the preparation is in the range 0.5 to 3 mm, more especially in the range 1 to 2 mm.

The preparation according to the invention preferably contains from 5 to 100 mg of ISMN or more especially 10 to 50 mg of ISMN.

The preparation according to the invention may also include an antimicrobial agent or a preservative. Suitable antimicrobial agents/preservatives include benzalkonium chloride, cetrimide (cetyltrimethylammonium bromide), benzoic acid, benzyl alcohol, Parabens (Trade Mark for the methyl-, ethyl-,propyl-and butyl-esters of para-hydroxybenzoic acid) chlorhexidine, chlorobutanol, phenylmercuric acetate, borate and nitrate, potassium sorbate, sodium benzoate, sorbic acid and thiomersal (mercurithiosalicylate) or a mixture thereof.

The preparation according to the invention may also include an antioxidant. Preferred antioxidants include sodium metabisulphite, butylated hydroxyanisole and butylated hydroxytoluene or a mixture thereof.

The preparation according to the invention may also include a pH-controlling agent. Preferred pH-controlling agents include citric acid and sodium citrate.

The preparation according to the invention may also include a plasticizer. Suitable plasticizers include diethylphthalate, dibutylphthalate and tributylcitrate or a mixture thereof.

The preparation according to the invention may. also include a surfactant. Suitable surfactants include sodium lauryl sulphate, diethylene glycol monostearate, propylene glycol monostearate, polyethylene glycols as sold under the Trade Mark MACROGOL, polysorbates and polyvinyl alcohol or a mixture thereof.

The preparation according to the invention may also include a penetration enhancer. Suitable penetration enhancers include dimethylsulphoxide, N, N-dimethylacetamide, N, N-dimethylformamide, 2-pyrrolidone, N-methyl-2-pyrrolidone and 1-dodecyl azacyclo-heptan-2-one or a mixture thereof.

The preparation according to the invention may also include a humectant. A particularly preferred humectant is glycerol for use in a high humidity environment. As indicated above glycerol may also be used as a solvent in forming the preparation according to the invention and when used as such will confer humectant properties on the preparation.

Further the preparation according to the invention may also include a local anaesthetic. Suitable local anaesthetics include lidocaine, benzocaine, lignocaine, methocaine, butylaminobenzoate and procaine or a mixture thereof. The preparation would include a local anaesthetic mainly to suppress irritation at the site of application thereof.

Additionally, the preparation according to the invention may include a rubefacient. Particularly preferred rubifacients include camphor and menthol or a mixture thereof and other locally acting peripheral vasodilators.

The preparation according to the invention is preferably applied to the flexor surface of the forearm, including the wrist, and also the ankle. Such sites of application show the greatest consistency from individual to individual in terms of ISMN absorption relative to other sites for administration because of the amount of tissue at such sites. Blood vessels are found close to the surface of the skin at such sites which facilitates the uptake of ISMN into the systemic circulation.

On contact of the preparation according to the invention with the skin, the ISMN starts to migrate rapidly from the preparation to the humid interface at the point of contact and then through the skin and into the bloodstream. The rate and extent of this percutaneous absorption is dependent on several factors including:
a) The amount of ISMN in the preparation.
b) The surface area of the preparation.

As it is the skin itself that forms the rate controlling barrier and not the dosage form comprising the preparation, the effect of ISMN loading will only be observed in terms of systemic ISMN levels below a threshold loading level.

Below this threshold the amount of ISMN in the dosage form is the factor which determines the concentration gradient that in turn controls the rate of absorption. Above this threshold increasing drug loading has no effect on absorption as the ability of the skin to absorb ISMN is saturated. However, such drug loading does have the effect of prolonging the time course of drug delivery by providing a larger drug depot. In order to increase the extent of absorption above the threshold it is necessary to increase the area of absorption by increasing the surface area of the dosage form so that a larger area of the skin is in contact with the ISMN.

The preparation according to the invention can be presented in a number of devices and dosage forms for the percutaneous administration of ISMN. These devices and dosage forms may contain an ISMN impermeable layer so as to cause unidirectional administration of ISMN through the skin from the surface of the preparation in the device or dosage form exposed to the skin. Such devices and dosage forms include, but are not limited to, a device known under name PANODERM and which is the subject of our EP-B-0 117 027, a device known under the name DERMAFLEX and which is the subject of our EP-B-0 113 562, self adhesive patches, bandages and plasters, creams, gels, jellies, mucilages, ointments and pastes. The term mucilaginous medium as used herein embraces creams, gels, jellies, ointments and pastes.

The preparation according to the invention may be adapted for reception in a receptacle of a device which can be held in contact with the skin.

Means for securing transdermal patches to the body include, apart from adhesive means, straps, bracelets and like securing devices.

The present invention is also designed to provide, through percutaneous administration by way of the said devices and dosage forms, a highly cosmetically and aesthetically acceptable method of easily and discreetly administering ISMN to a patient in need of such treatment.

With the present invention, it is possible to affix one of the said devices or dosage forms to the skin, so as to provide controlled absorption of ISMN through the skin directly into the bloodstream, maintaining maximum effective levels of ISMN in the blood between 2 and 16 hours and achieving minimum effective blood levels from 12 to 20 hours over a 24 hour period.

Preferably, minimum effective blood levels are achieved from 14 to 18 hours over a 24 hour period.

In order to form the preparation according to the invention the thickening, hardening, setting, gelling, suspending or solidifying agent or a mixture of such agents is added to the solvent(s) at a concentration that will result in a suitably mucilaginous, semi-solid or solid mass. The mixture is mixed and/or heated, depending on the agent used, so as to produce a uniform medium. The ISMN is added to produce a concentration suitably in the range 0.5% to 25%, and preferably in the range 1% to 10%. Any other inactive ingredients and additional ingredients as hereinbefore specified are now added and the entire mixture is mixed to uniformity. This mixture is now used to form the final dosage form which may be any of the following:

a) a solid or semi-solid disc or patch formed by moulding, cutting, punching or slicing of the mixture.
b) a cream.
c) a mucilage.
d) a gel.
e) a paste.
f) a jelly.
g) an ointment.

The dosage form may now be incorporated into any suitable device for attachment to the skin as indicated above.

According to a further aspect of the invention there is provided use of a drug for the manufacture of a pharmaceutical formulation for use in the once-daily administration of said drug in a method to inhibit the development of drug tolerance in humans being treated with said drug in which the once-daily formulation is adapted to achieve therapeutically effective levels of said drug in the blood over a period of not more than 20 hours of the day and further adapted to cause said blood levels to fall significantly below said therapeutic levels throughout the remainder of the 24 hour period.

Preferably, the drug is in the form of a pellet formulation or preparation according to the invention as hereinabove specified. The drug is suitably an ISMN or a pharmaceutically acceptable salt thereof.

DETAILED DESCRIPTION OF THE INVENTION

The invention will be further illustrated by the following Examples.

EXAMPLE 1

Controlled Absorption Isosorbide-5-mononitrate

Fumaric acid (4 kg) was size reduced in a conventional pharmaceutical hammer mill through a No. 100 mesh screen. The milled fumaric acid was then blended with isosorbide-5-mononitrate (5 kg) (80% in lactose) for twenty minutes. A solution of polyvinylpyrrolidone (P.V.P.) and ethylcellulose in isopropanol was prepared at concentrations of 16.0% and 1.25% of the respective components.

Non-pareil seeds (5 kg) with a particle size of 0.6 to 0.71 mm were placed in a conventional pharmaceutical coating pan. The fumaric acid/isosorbide-5-mononitrate/lactose blend was applied onto the non-pareil seeds using the P.V.P./ethylcellulose solution as a binding agent. On completion of this operation the resulting active cores were transferred to a tray drying oven for solvent removal. The oven temperature was set at 55° C. and the drying time was not less than 12 hours.

A solution containing 1.7% of P.V.P. and 10.4% of ethylcellulose in isopropanol was prepared. To this mixture was added talc at a concentration of 28% weight per weight. The active cores were removed from the oven and transferred to a suitable coating pan. An aliquot of the polymer and talc suspension consisting of 10 g of suspension per kg of active cores was applied to the active cores in the coating pan. Adequate drying time, typically between 5 and 20 minutes, was allowed between the application of this aliquot. At specified intervals the product was removed from the coating pan and transferred to the tray drying oven for drying of duration not less than 12 hours at 50° C.

The formulation as described above when tested in vivo in human volunteers gave a plasma profile as hereinabove specified.

EXAMPLE 2

Example 1 was repeated except the following quantities and materials were used; Fumaric acid (4 kg) was replaced by lactose (3 kg), non-pareil seeds, 0.4–0.5 mm (4 kg), isosorbide-5-mononitrate (80% in lactose) (6 kg). A solution of polyvinylalcohol and cellulose acetate in acetone/isopropanol 40/60 at concentrations of 10% and 2% respectively was used to apply the drug excipient blend on to the non-pareil seeds. After drying, a polymeric solution containing suspended material was applied to the active cores as described in Example 1. This suspension consisted of EUDRAGIT RS, EUDRAGIT RL and EUDRAGIT L in an acetone/isopropanol mixture 40/60 at concentrations of 5%, 5% and 2.5% respectively, to which was added 2.5% tributyl citrate and 25% magnesium stearate. The resulting membrane suspension was applied to the active cores as described in Example 1.

EXAMPLE 3

Example 1 was repeated except fumaric acid was replaced by talc.

EXAMPLE 4

Example 1 was repeated except fumaric acid was replaced by citric acid (2 kg).

EXAMPLE 5

Example 2 was repeated except the suspension applied to the active cores was replaced by: cellulose acetate and cellulose acetate phthalate in acetone at concentrations of 10% and 3% respectively, with talc replacing the magnesium stearate and dibutyl sebecate replacing the tributyl citrate.

EXAMPLE 6

Controlled Absorption Isosorbide-2-mononitrate

Fumaric acid (4 kg) was size reduced in a conventional pharmaceutical hammer mill through a No. 100 mesh screen. The milled fumaric acid was then blended with isosorbide-2-mononitrate (5 kg) (80% in lactose) for twenty minutes. A solution of polyvinylpyrrolidone (P.V.P.) and ethylcellulose in isopropanol was prepared at concentrations of 16.0% and 1.25% of the respective components.

Non-pareil seeds (5 kg) with a particle size of 0.6 to 0.71 mm were inserted into a CF granulator which has the advantage of automating the process that is performed in pan coating. The fumaric acid/isosorbide-2-mononitrate/lactose blend was applied onto the non-pareil seeds using the P.V.P./ethylcellulose solution as a binding agent. On completion of this operation the resulting active cores were transferred to a tray drying oven for solvent removal. The oven temperature was set at 50° C. and the drying time was not less than 12 hours.

A solution containing 1.7% of P.V.P. and 10.4% of ethylcellulose in isopropanol was prepared. The active cores were removed from the oven and transferred to a CF granulator. A membrane was applied to the active cores by spraying on the polymer suspension, while simultaneously but separately dusting on talc in conventional manner. At specified intervals the product was removed from the granulator and transferred to the tray drying oven for drying of duration not less than 12 hours at 50° C.

The formulation as described above when tested in vivo in human volunteers gave a plasma profile as hereinabove specified.

EXAMPLE 7

Example 6 was repeated except the drug excipient blend was applied onto the non-pareil core using an aqueous dispersion of hydroxypropyl methylcellulose 5% and ethylcellulose 1%, triethyl citrate 1.5% and talc 1%. The membrane suspension applied to the active cores consisted of EUDRAGIT RS 30D and EUDRAGIT RL 30D at concentrations of 10% and 2.5% respectively. To this aqueous dispersion was added 2.5% diethylphthalate and 10% talc.

EXAMPLE 8

Example 6 was repeated except fumaric acid was replaced by sorbitol (1 kg).

EXAMPLE 9

Example 1 was repeated except fumaric acid was replaced by succinic acid.

EXAMPLE 10

To 2.5 g of carrageenan, 50 ml of water was added. The solution was heated and stirred until the gel was fully dissolved. 4.0 g of IS-2-MN was dissolved in 50 ml ethanol and added slowly to the dissolved carrageenan solution. When the liquid mixture was fully uniform, it was poured into a cylindrical mould having a diameter of 3.00 cm. The liquid was allowed to cool and solidify at room temperature. Discs weighing 1 g (±5%) were cut from the solid gel, mounted on an occlusive dressing and sealed in aluminium foil to prevent dehydration. Each disc contained 40 mg IS-2-MN.

EXAMPLE 11

1 g of IS-2-MN was dissolved in 25 ml of water. 0.625 g of carrageenan was added and the mixture was heated to dissolve the carrageenan. The solution was then poured into a cylindrical mould having a diameter of 2.12 cm and allowed to cool and solidify at room temperature. Discs weighing 500 mg (±5%) were cut from the solid gel, mounted on an occlusive dressing and sealed to prevent dehydration. Each disc contained 20 mg IS-2-MN.

EXAMPLE 12

A device was prepared as in Example 11 with 0.5 g of IS-2-MN added to 25 ml of water. Each disc contained 10 mg IS-2-MN.

EXAMPLE 13

To 2.5 g xanthan gum, 75 ml of water was added and the gum was allowed to dissolve fully aided by heat and agitation. A separate solution was prepared containing 2.5 g IS-2-MN dissolved in 20 ml water to which 25 ml propylene glycol was added. The resulting mixture was added to the xanthan gum solution using heat to aid uniform mixing. This mixture was poured while warm into a circular mould with a diameter of 5 cm. The liquid was allowed to cool and solidify at room temperature and discs were cut having a dose equivalent to 50 mg per patch. The discs were packaged in a hermetically sealed pouch. Backing materials were supplied to ensure that the device, when applied, remained at the site of application.

EXAMPLE 14

Example 13 was repeated except karaya gum (3.5 g) replaced the xanthan gum and glycerol replaced the propylene glycol.

EXAMPLE 15

Example 10 was repeated except carageenan was replaced by agar.

EXAMPLE 16

1 g of IS-2-MN was dissolved in 10 ml ethanol. The resulting solution was emulsified using a silicone polymeric phase as the external phase. After the internal phase droplets had achieved a particle size of less than 200 microns, a hardening agent was added and the material was poured into a circular mould having a diameter of 2 cm. This was then heated at 40° C. to ensure completion of the hardening process. Thereafter discs were prepared containing 25 mg IS-2-MN and packed individually in suitably sealed pouches.

EXAMPLE 17

Example 16 was repeated except propylene glycol replaced the ethanol.

ISMN Oral Formulation In-Vivo Studies

Steady state in-vivo studies were performed in healthy volunteers ranging in age from 19 to 33 years. The study was conducted to examine the pharmacokinetic characteristics of the formulation of Example 1. The subjects received orally, once-daily, 40 mg of a capsule formulation of ISMN pellets prepared according to Example 1.

Blood samples were obtained from each subject before administration of medication on days 1, 2, 3, 4 and 5. On day 5, blood samples were obtained from each subject at the following times after administration of medication: 0.5, 1, 1.5, 2, 3, 4, 6, 8, 10, 12, 12.5, 13, 13.5, 14, 15, 16, 20, 24, 36 and 48 hours. Plasma was obtained by centrifugation of the blood samples at 2° C. and IS-5-MN levels were measured by a capillary gas chromatography method. The results obtained with the formulation as described in Example 1 demonstrated a mean Tmax at 3 hours of approximately 320 ng/ml.

This study also demonstrated the rapid attainment of appreciable IS-5-MN plasma levels followed by a washout period, where the IS-5-MN plasma concentration fell from 320 ng/ml to well below 100 ng/ml. The peak-to-trough ratio obtained was 6.5:1.

ISMN Transdermal In-Vivo Studies

In-vivo studies were performed in healthy volunteers ranging in age from 24 to 33 years. The ISMN discs were prepared according to Example 10. The patches were applied to the volar aspect of the forearm at 0 hours. Blood samples were obtained at 0 hours immediately before the dosage form was applied onto the skin and at specific times thereafter. Plasma was obtained by centrifugation of the blood samples at 2° C. and IS-2-MN levels were measured by a capillary gas chromatography method. The results obtained with the preparation as described in Example 10 demonstrated a mean Tmax at 12 hours of approximately 24 ng/ml.

This study also demonstrated the rapid attainment of appreciable IS-2-MN plasma levels followed by a washout period, where the IS-2-MN plasma concentration fell from 24 ng/ml to below 20 ng/ml. The peak-to-trough ratio attained was 12:1.

What is claimed is:

1. A controlled-release pharmaceutical formulation for once-per-day oral administration, comprising spheres having a core including sugar spheres or nonpareils coated with an isosrbide mononitrate; and a diffusion control membrane surrounding the core comprising a pharmaceutically acceptable, film forming polymer, the film forming polymer being present in an amount effective to permit release of the isosrbide monoitrate from the spheres, over a 24 hour dosing period, at a rate of release that achieves a therapeutically effective level of the isosrbide monoitrate for at least 12 hours after administration of the pharmaceutical formulation, while providing less than therapeutically effective levels of the at least one isosrbide monoitrate for the remainder of the 24 hour dosing period so as not to induce tolerance in a patient administered the pharmaceutical formulation once every 24 hours.

2. The controlled release pharmaceutical formulation of claim 1, wherein said film forming polymer permits release of said isosrbide monoitrate at a rate that achieve a therapeutically effective level of the isosrbide monoitrate for at least 14 hours.

3. The controlled release pharmaceutical formulation of claim 1, wherein said film forming polymer permits release of said isosrbide monoitrate at a rate that achieves a therapeutically effective level of the isosrbide monoitrate for at least 18 hours.

4. The controlled release pharmaceutical formulation of claim 1, wherein said drug is an organic nitrate.

5. The controlled release pharmaceutical formulation of claim 1, wherein said formulation includes a seal coat formed over said core.

6. A controlled-release pharmaceutical formulation for once-per-day oral administration, comprising sugar spheres or nonpareils including an isosorbide mononitrate; and a diffusion control membrane surrounding the spheres or nonpareils comprising a pharmaceutically acceptable, film forming polymer, the film forming polymer being present in an amount effective to permit release of the isosorbide mononitrate from the sugar spheres or nonpareils, over a 24 hour dosing period, at a rate of release that achieves a therapeutically effective level of the isosorbide mononitrate for at least 12 hours after administration of the pharmaceutical formulation, while providing less that therapeutically effective levels of the isosorbide mononitrate for the remainder of the 24 hour dosing period so as not to induce tolerance in a patient administered the pharmaceutical formulation once every 24 hours.

7. The controlled release pharmaceutical formulation of claim 6, wherein said formulation includes a seal coat formed over said core.

8. A method of preventing the onset of nitrate tolerance in a human undergoing nitrate therapy, which comprises:

administering a tablet or capsule containing an isosrbide monoitrate blended with nonpareils or sugar spheres, to the human over a 24 hour dosing period so as to achieve therapeutically effective levels of the an isosrbide monoitrate about 12 hours, followed by less than therapeutically effective levels of the isosrbide monoitrate for the remainder of the 24hour dosing period.

9. The method of claim 8, wherein said tablet or capsule achieves therapeutically effective levels of the isosrbide monoitrate for at least about 14 hours.

10. The method of claim 8, wherein said tablet or capsule achieves therapeutically effective levels of the isosrbide monoitrate for at least about 18 hours.

11. A method of treating a human with an isosrbide monoitrate without inducing nitrate tolerance, which comprises:

administering a tablet or capsule containing at least one isosrbide monoitrate blended with nonpareils or sugar spheres, to the human over a 24 hour dosing period so as to achieve therapeutically effective levels of the isosrbide monoitrate for at least about 12 hours, followed by less than therapeutically effective levels of the isosrbide monoitrate for the remainder of the 24 hour dosing period.

12. The method of claim 11, wherein said tablet or capsule achieves therapeutically effective levels of the isosrbide monoitrate for at least about 14 hours.

13. The method of claim 11, wherein said tablet or capsule achieves therapeutically effective levels of the isosrbide monoitrate for at least about 18 hours.

14. The method of claim 11, wherein the isosrbide monoitrate is isosorbide-2-mononitrate, or isosorbide-5-mononitrate.

15. The method of claim 14, wherein the isosorbide-5-mononitrate comprises an isosorbide-5-mononitrate triturate.

16. The method of claim 15, wherein the isosorbide-5-mononitrate triturate includes a member selected from the group consisting of lactose, mannitol, and mixtures thereof.

17. A method of treating a human by the once-per-day oral administration of organic nitrate comprising: orally administering once during each 24 hour time period a controlled-release organic nitrate formulation comprising spheres having a core including sugar spheres coated with an isosorbide mononitrate; and a diffusion control membrane surrounding said core comprising a pharmaceutically acceptable, film forming polymer, the film forming polymer being present in an amount effective to permit release of the isosorbide mononitrate from said spheres, over a 24 hour dosing period, at a rate of release that achieves a therapeutically effective level of the isosorbide mononitrate for at least 12 hours after administration of the formulation, while providing less than therapeutically effective levels of the isosorbide mononitrate for the remainder of the 24 hour dosing period so as not to induce nitrate tolerance in a human patient administered the nitrate formulation once every 24 hours.

18. The method of claim 17, wherein a seal coat is formed over said core.

* * * * *